(12) United States Patent
Reaux et al.

(10) Patent No.: US 10,342,607 B1
(45) Date of Patent: Jul. 9, 2019

(54) ELECTRO-SURGICAL PENCIL WITH AN ADJUSTABLE VACUUM NOZZLE

(71) Applicants: Brian K Reaux, Red Oak, TX (US); Quedon J Baul, McKinney, TX (US)

(72) Inventors: Brian K Reaux, Red Oak, TX (US); Quedon J Baul, McKinney, TX (US)

(73) Assignees: Brian K. Reaux, Red Oak, TX (US); Quedon Baul, Dallas, TX (US)

( * ) Notice: Subject to any disclaimer, the term of this patent is extended or adjusted under 35 U.S.C. 154(b) by 209 days.

(21) Appl. No.: 15/227,039

(22) Filed: Aug. 3, 2016

Related U.S. Application Data (60) Provisional application No. 62/282,568, filed on Aug. 4, 2015.

(51) Int. Cl.
  *A61B 18/14* (2006.01)
  *A61B 18/12* (2006.01)
  *A61B 18/00* (2006.01)

(52) U.S. Cl.
  CPC ...... *A61B 18/1485* (2013.01); *A61B 18/1206* (2013.01); *A61B 2018/00589* (2013.01); *A61B 2018/00601* (2013.01); *A61B 2018/1412* (2013.01); *A61B 2218/008* (2013.01)

(58) Field of Classification Search
  CPC .............. A61B 2218/008; A61B 18/14; A61B 18/1485; A61B 2018/00589; A61B 2018/00607; A61B 2018/1412; A61B 17/00; A61M 1/0031
  See application file for complete search history.

(56) References Cited

U.S. PATENT DOCUMENTS

| | | | | |
|---|---|---|---|---|
| 4,550,739 A | * | 11/1985 | Henderson | A24F 9/10 131/243 |
| 4,963,134 A | * | 10/1990 | Backscheider | A61M 1/0023 55/467 |
| 5,061,268 A | * | 10/1991 | Fleenor | A61B 18/042 606/45 |
| 5,154,709 A | * | 10/1992 | Johnson | A61B 18/1402 604/35 |

(Continued)

OTHER PUBLICATIONS

UNK., The Perfect Balance of Precision and Protection, Outpatient Surgery, Internet, Stryker Medical, Neptune E-SEP, Jul. 20, 2016, 2 pgs.

(Continued)

*Primary Examiner* — Thomas A Giuliani
*Assistant Examiner* — Catherine Premraj (57) ABSTRACT

An electro-surgical pencil with a vacuum for removing surgical plume. On the proximal end of the elongated housing are electrical wires and a vacuum tube. These are connected into a control and a source of vacuum. The distal end has a blade for cutting and coagulation. A vacuum nozzle is positioned about the blade and is translatable in the housing. A push bar control or slider on the housing moves the vacuum nozzle from an on-position where it is connected to the external source of vacuum and leaves the blade substantially exposed. In an off-position, the vacuum tube has a disconnectable joint that has a fitting that is removed from the vacuum tube. The external nozzle in this off-position substantially covers the blade. The push bar control may act as a control of the electrical and vacuum sources. The pencil is sterilized and disposable.

6 Claims, 7 Drawing Sheets

(56) References Cited

U.S. PATENT DOCUMENTS

| | | | | |
|---|---|---|---|---|
| 5,460,602 | A | * 10/1995 | Shapira | A61B 18/1402 604/119 |
| 7,241,294 | B2 | 7/2007 | Reschke | |
| 7,244,257 | B2 | 7/2007 | Podhajsky | |
| 7,959,633 | B2 | 6/2011 | Sartor et al. | |
| 8,128,622 | B2 | 3/2012 | Podhajsky et al. | |
| 8,663,219 | B2 | 3/2014 | Heard et al. | |
| 2009/0248008 | A1* | 10/2009 | Kerr | A61B 18/1402 606/34 |
| 2011/0190768 | A1* | 8/2011 | Shvetsov | A61B 18/18 606/48 |
| 2012/0171055 | A1* | 7/2012 | Wisniewski | A61M 1/0041 417/234 |
| 2012/0203223 | A1* | 8/2012 | Terry | A61B 18/1402 606/42 |
| 2015/0209100 | A1* | 7/2015 | Ineson | A61B 18/1402 606/42 |

OTHER PUBLICATIONS

Rudolph, "Solutions for Surgical Plume," Surgical Products mag., Jul./Aug. 2015, pp. 16-21, US.

* cited by examiner

ELECTRO-SURGICAL PENCIL WITH AN ADJUSTABLE VACUUM NOZZLE

CROSS REFERENCES TO RELATED APPLICATIONS

This is a regular filing of Ser. No. 62/282,568, filed Aug. 4, 2015, entitled "Electro surgical pencil", by the same inventor and is incorporated herein.

Reference to Federally sponsored research or development: NA

Reference to joint research agreements: NA

Reference to Sequence Listing: NA

BACKGROUND OF THE INVENTION

Field of the Invention

The present invention relates generally to surgical tools, and, more particularly, relates to surgical tools for cutting tissue, and, in greater Particularity, relates to electrical cutting devices for cutting tissue and thus creating surgical plume.

Description of the Prior Art

Surgical plume results from surgical and laser procedures. The surgical plume carries chemicals resulting from the burning of human body parts as well as other molecular products such as water, germs, etc., which flow away from the operating site on the body and thus expose not only the patient but operating room staff to possibly deadly contamination. Several methods and devices are presently used to remove this contamination.

A brief explanation of this problem is contained in an article titled, "Solutions for Surgical Plume" by Rebecca Rudolph published in Surgical Products, issue July/August 2015 at pages 14 to 18. Additionally, several surgical pencils are shown that address this issue.

The following U.S. Pat. Nos. 5,061,268; 7,241,294; 7,244,257; 7,959,633; 8,128,622; and 8,663,219 are incorporated by reference.

One manufacturer of a surgical Pencil called the "Neptune E-SEP Smoke Evacuation Pencil"™ is Styker Medical and is shown on the Internet. The blade is surrounded by a smoke evacuation tube that is non-movable.

These products and patents are incorporated by reference as prior art.

Accordingly, there is a need for an improved electro-surgical pencil for removing plume.

SUMMARY OF THE INVENTION

The present invention provides an improved surgical pencil having an adjustable vacuum to remove containments known as plume.

An electro-surgical pencil with a vacuum for removing surgical plume. On the proximal end of the elongated housing are electrical wires and a vacuum tube. These are connected into a control and a source of vacuum. The distal end has a conventional blade for cutting and coagulation. A vacuum nozzle is positioned about the blade and is translatable in the housing. A push bar control on the housing moves the vacuum nozzle from an on-position where it is connected to the external source of vacuum and leaves the blade substantially exposed. In an off-position, the vacuum tube has a disconnectable joint that has a fitting that is removed from the vacuum tube. The external nozzle/shield/guard in this off-position substantially covers the blade. The push bar control may act as a control of the electrical and vacuum sources. Additional features may include a light source at the distal end of the pencil and a filter in the vacuum line to remove containments. The pencil is sterilized and disposable.

An object of the present invention is to provide an improved surgical pencil.

It is another object of the present invention to provide an improved surgical pencil providing a source of vacuum to remove surgical, plume.

It is a further object of the present invention to provide an improved surgical pencil providing a source of variable vacuum to remove surgical plume.

It is still a further object of the present invention to provide an improved surgical pencil providing a disconnectable source of vacuum to remove surgical Plume.

It is still another object of the present invention to provide an improved surgical pencil providing a source of vacuum to remove surgical plume incorporated within the housing of the pencil that is controlled by a slider on the housing.

It is still another object of the present invention to provide an improved surgical pencil providing a source of vacuum to remove surgical plume incorporated within the housing of the pencil that can be sterilized and disposable.

It is still another object of the present invention to provide an improved surgical pencil providing a source of vacuum to remove surgical plume incorporated within the housing of the pencil such that the suction sounds is integral thereto.

It is still another object of the present invention to provide an improved surgical pencil providing a source of vacuum to remove surgical plume incorporated within the housing of the pencil and having a source of light therein.

It is still another object of the present invention to provide an improved surgical pencil providing a source of vacuum to remove surgical plume incorporated within the housing of the pencil and having a movable guard/shield about the blade with a partial roof thereon.

These and other objects, features, and advantages of the present invention will become more readily apparent from the attached drawings and the detailed description of the preferred embodiments, which follow.

Like reference numerals refer to like parts throughout the several views of the drawings. In the description and drawings that follows, "proximal" refers to the position where the operator's hand holds the pencil, and the "distal" position as being located near or at the end of the pencil with the blade. Normally proximal would be on the right side position of the drawings and distal on the left side position.

DETAILED DESCRIPTION OF THE PREFERRED EMBODIMENTS

Removing the surgical Plume created during surgery by a surgical pencil is an important safety issue being addressed by the present invention.

Although at least one detailed embodiment is given herein, equivalent structures may be used in place thereof as would be known to one skilled in the art after reading and understanding the present invention.

In general, an electro-surgical pencil with an adjustable vacuum removes surgical plume. On the proximal end of the elongated housing are electrical wires and a vacuum tube. These are connected into a control and a source of vacuum. The distal end has a conventional blade for cutting and coagulation. A vacuum nozzle is positioned about the blade and is translatable in the housing and over the blade. A push bar control or slider is mounted on the housing and moves the vacuum nozzle from an on-position where it is connected to the external source of vacuum and leaves the blade substantially exposed. In an off-position, a disconnectable joint has a fitting that is removed from the vacuum tube. The external nozzle in this off-position substantially covers the blade. The push bar control may act as a control of the electrical and vacuum sources. The push bar control may be variable. The pencil is sterilized and disposable due to the containments release during surgery.

Figure 1:
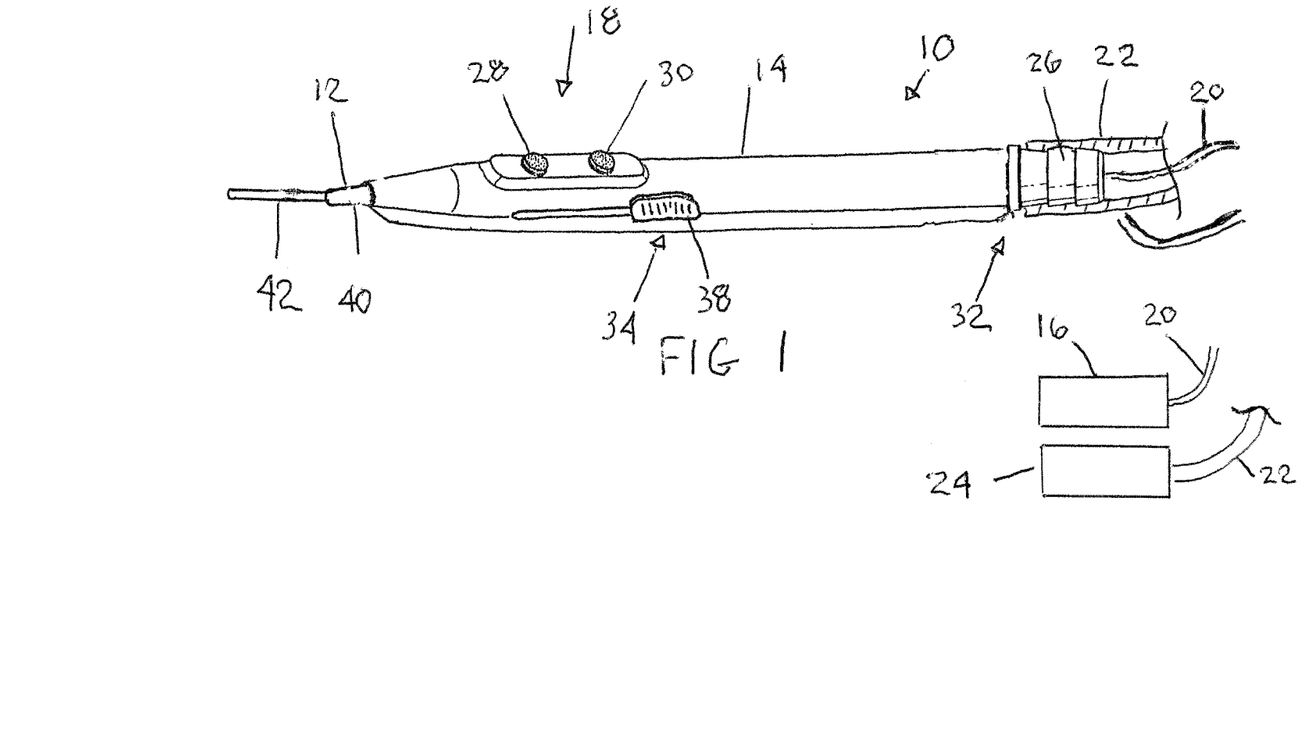
FIG. 1 is a perspective view of the surgical pencil with the movable guard retracted into the housing of the present invention.

FIG. 1 is a perspective view of the surgical pencil 10 with a movable guard/shield/nozzle 12 retracted into an elongated, pencil-shaped housing 14 that may be held by one hand of an operator such as a surgeon. An electrical means 16 for powering the surgical pencil 10 includes a source of power 16 such as an AC/DC converter and a control means 18 such as a cutting on-off switch 28 and a coagulating switch 30 connected to the electrical means 16 by one or more wires 20 as is well known in the art. The wires 20 may enter the pencil 10 through a vacuum line 22 to minimize attached loose lines and wires. A surgical blade 42 is mounted in a distal end of said surgical pencil 10. The surgical blade 42 is operably connected to the electrical means for selectively receiving power from said control means to either cut or coagulate a human body part.

A vacuum source 24 provides a vacuum to the surgical pencil 10 through the vacuum line 22 attached to a male nipple 26 on a proximal end 32 of the surgical pencil 10. The vacuum source 24 may have a vacuum control 50, FIG. 7, mounted on the vacuum line 22 having a button switch 52 or mounted in the housing 14, and may further operate by a first push turning on the vacuum source 24, a second push adjusting the vacuum to a medium level, a third push adjusting the vacuum to a high level and a fourth push turning off the vacuum source 24.

A slider 38 may be used to adjust the vacuum in the elongated housing 14. A vacuum control 34 for adjusting the vacuum on the surgical pencil 10 has a disconnectable coupling 36, FIG. 3, inside the elongated housing 14 with a slider or push bar switch 38 as will be further described below as well as other control means either attached to the housing 14 or to a vacuum line 22, FIG. 7. A shield/guard/nozzle 12 is mounted in the elongated housing 14 and the shield 12 comprises cylindrical tube 40 having a portion of a blade 42 therein. The slider switch 38 is fixedly mounted to the shield 12 as will be further explained hereinbelow.

Figure 2:
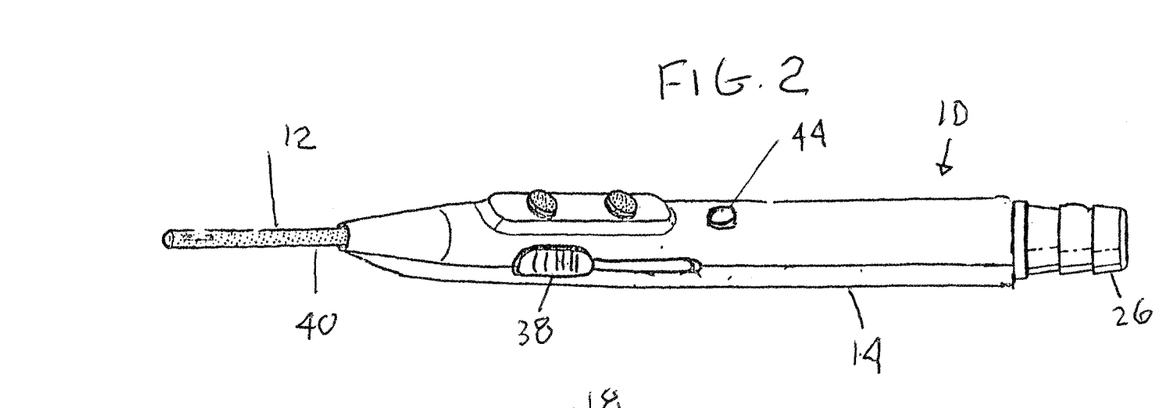
FIG. 2 is a perspective view of the surgical pencil of FIG. 1 with the movable guard extended from the housing of the present invention.

FIG. 2 is a partial perspective view of the exterior of the surgical pencil 10 with the movable guard slider 38 in the extended position in the housing 14 of the present invention. The moving guard 40 completely covers the blade 42 as seen in FIG. 1, but it may also partially cover the blade 42. The movable guard 40 would be made from a heat resistant material such as plastic and may be clear plastic to allow the position of the blade 42 seen therein. In one embodiment the wires 20 may come out of the male nipple 26 and have a connector thereon that would connect to the wires from the power source 16 and vacuum source 24 placed inside on the vacuum line 22. Once connected, the vacuum line 22 would be attached to the male nipple 26 so as to minimize the initial setup.

Figure 3:
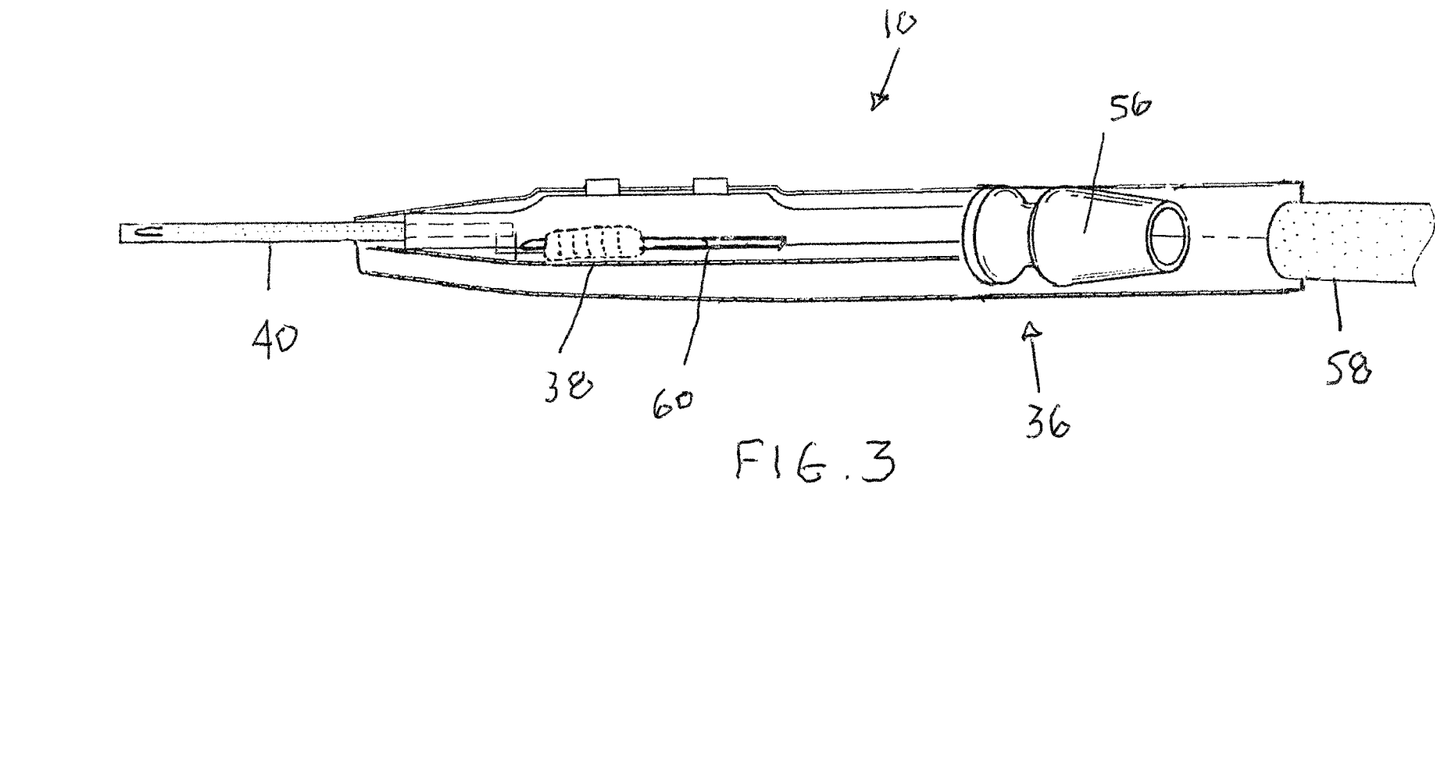
FIG. 3 is a partial perspective view of the interior of the surgical pencil with the movable guard slider in the off position, guard extended, and the vacuum coupler disconnected, of the present invention.
Figure 4:
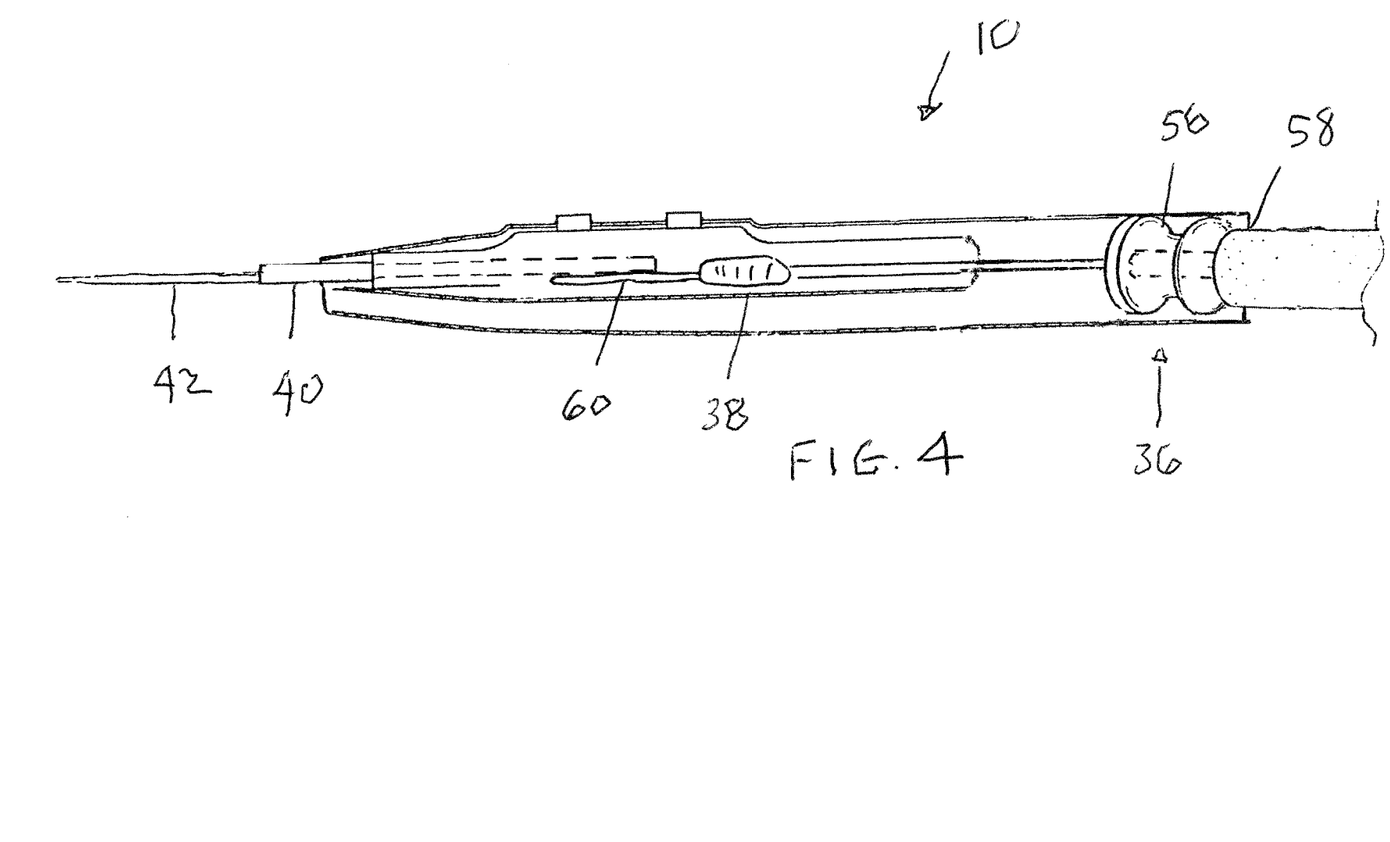
FIG. 4 being similar to FIG. 3 is a perspective view of the surgical pencil with the movable guard retracted into the housing to partially and substantially uncover the blade of the present invention with a maximum amount of vacuum when the coupler is connected.

FIG. 3 is a partial perspective view of the interior of the surgical pencil 10 with the movable guard slider 38 in the off position and the vacuum coupler 36 disconnected. The embodiment shown in FIGS. 3 and 4 present mechanical means to vary the vacuum and at the same time move the shield 40 from the blade 42. The vacuum coupling 36 comprises a conical male plug 56 and a female seat 58 being the first coupling end. In another embodiment the plug 56 may be just a pure stop so that when it is moved onto the seat 58, the vacuum totally stops. The conical male plug 56 provides a varying source of vacuum as it moves into the seat 58. When it is totally removed there is no vacuum until the vacuum source 24 is turned on. When the vacuum source 24 is turned on, a maximum vacuum will be present in the housing 14, but the shield 40 must then be removed from the blade 42 to suction up plume. This maximum vacuum will occur until the conical male plug is in very close proximity to the seat 58 as shown in FIG. 4. At this Point the shield 40 will be substantially removed from the blade 42. The shield 40 is attached to the slider button 38 and the slider button 38 translates within a slot 60 within the elongated housing 14. When the slider button 38 is fully to the right side or proximal side of the slot 60 there will be no vacuum, but as the plug 56 starts to enter into the seat 58, the amount of vacuum decreases this is due to the conical shape of the plug 56. In effect, the operator/doctor can turn off the vacuum with the coupling 36 closed. Also, the vacuum can be turned off by the vacuum on-off button 44 shown in FIG. 2. FIG. 4 shows the conical male plug 56 engaged to the seat 58. In another embodiment, the vacuum will only be present when the conical male plug 56 is engaged to the seat 58 wherein the vacuum is turned on by the slider button 38 being in or near the end of the right hand side of the slot 60 and there is a channel or hole through the conical male plug 56. In this embodiment the plug 56 need not be conical as the vacuum will be zero to maximum. Moving the shield 40 over the blade 42 would turn off vacuum. This control will be further discussed below.

Figure 5:
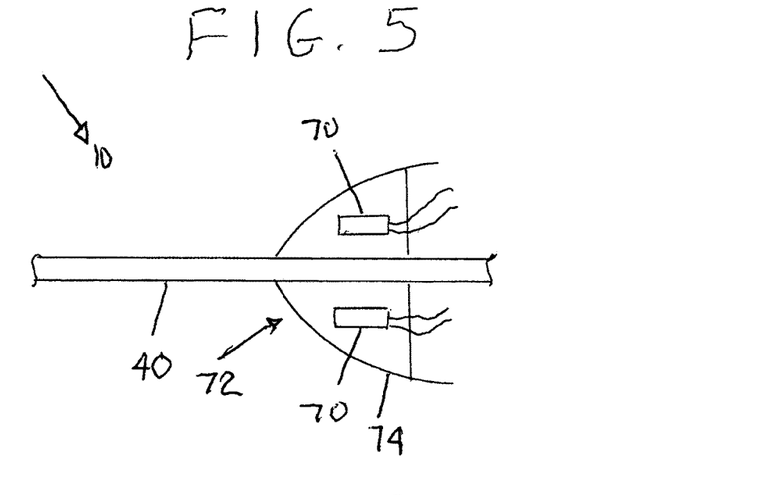
FIG. 5 is a perspective view of the surgical pencil having one or more lights about the tip the housing of the present invention.

FIG. 5 is a perspective view of the surgical pencil 10 having supplemental lights 70 located in the distal end 72 of the elongated housing 14. The distal end may be a clear plastic lens 74. The lights 70 may be LEDs or other small lights to fit in the tip of the elongated housing 14 of the surgical pencil 10. Wires 76 therefrom would connect into the power source 16 and pass through the switches 28 and 30 as noted above.

Figure 6:
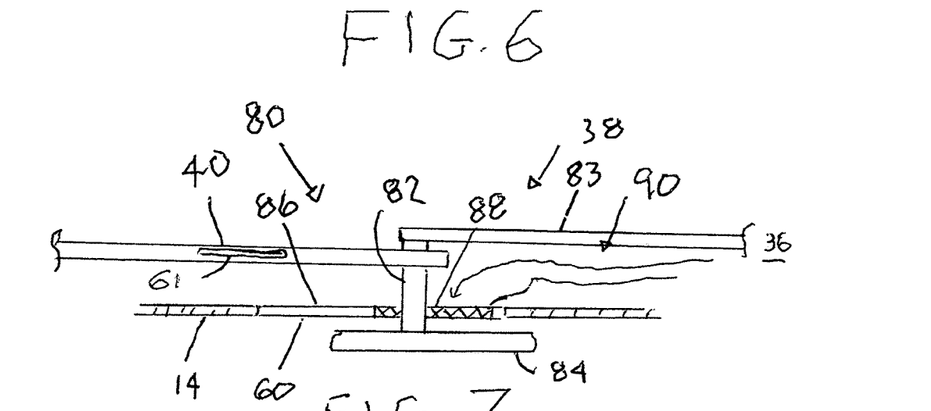
FIG. 6 is a perspective view of the surgical pencil with a variable vacuum control on the slider of the present invention.

FIG. 6 is a perspective view of the surgical pencil 10 with a variable vacuum control 80 on the slider 38 of the present invention. As seen therein, a partial end view of the shield 40 is shown connected by a bridge 82 to the slider button 84. By further design, the slider button 84 may be made into a clip for attaching the pencil 10 into or onto clothing. The housing 14 is shown by cross section and the slot 60 is shown. A bottom edge 86 of the slot 60 is shown. A rear portion of the bottom edge 86 is covered by a metal strip 88 with a similar metal strip placed on the top edge, not shown. The metal strips may include ridges so as to produce a tactile feel as the slider button is moved. The bridge 82 is conductive and thus current will flow in wires 90. The wires 90 may be connected to the very rear edge of the strips 88 and thus as the bridge 82 moves, the amount of resistance changes which can be detected by conventional electronics. The changing resistance can thus adjust the vacuum level. The bridge 82 is further connected to the vacuum coupler 36 by a coupler arm 83 so moving the slider 84 moves also the shield 40 and the male plug 56 in the same direction. As a result if the slider 84 is fully to the left, the shield 40 will substantially cover the blade 42 and the male plug 56 will not be seated and there should be no vacuum.

Figure 7:
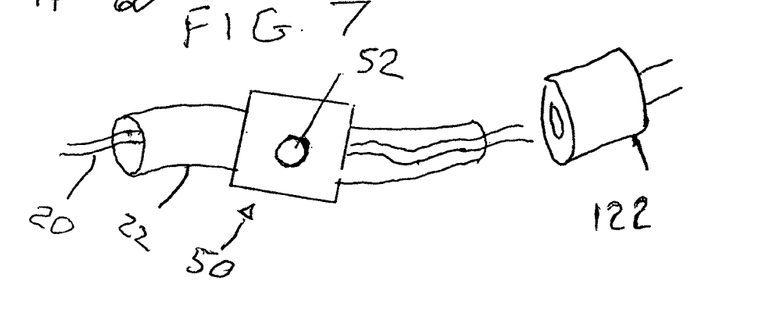
FIG. 7 is a partial side view of a vacuum control mounted to the vacuum hose of the surgical pencil of the present invention.

FIG. 7 is a partial side view of a vacuum control 50 mounted to the vacuum hose 22 of the surgical pencil 10 of the present invention. As noted previously, the vacuum control could be mounted in the elongated housing, and it could be mounted separated or even be a wireless controller such as a TV remote.

Figure 10:
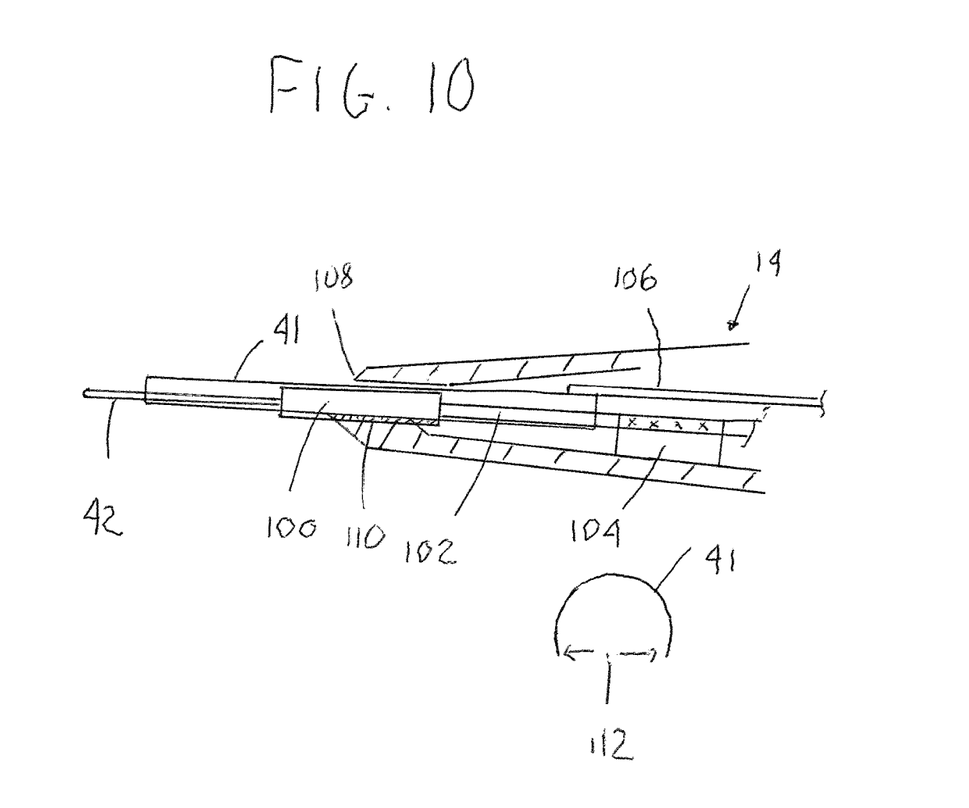
FIG. 10 is a Partial side view of an elongated housing having a C-shaped shield 41 about the blade 42 of the present invention.
Figure 11:
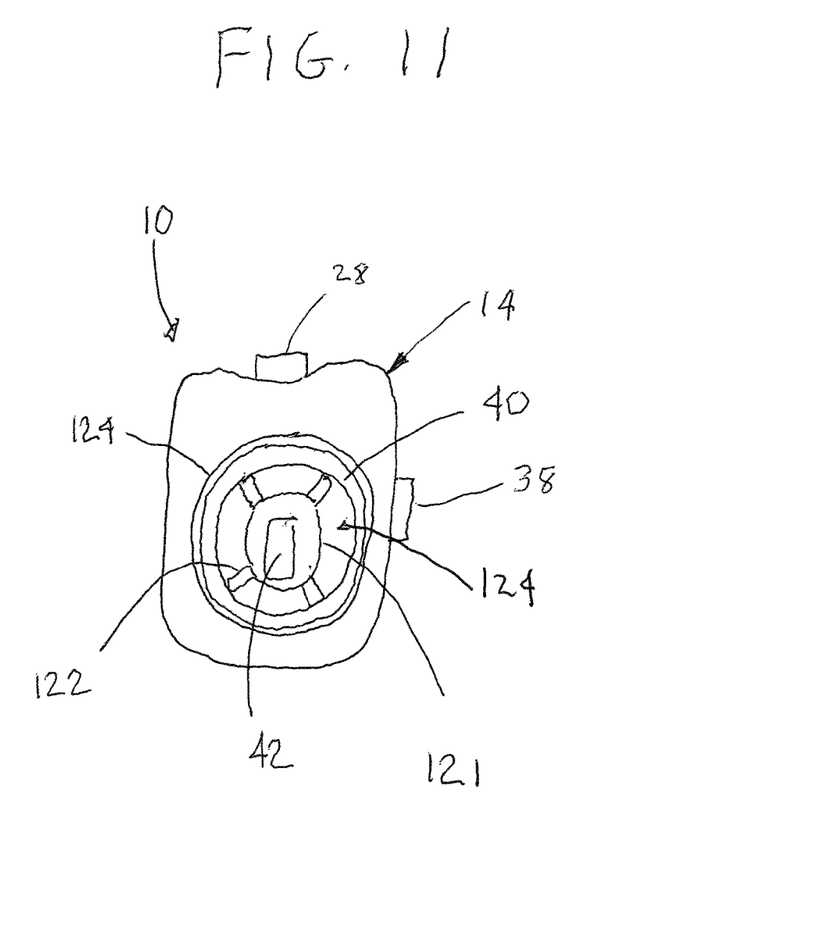
FIG. 11 is a front view of the surgical pencil of the present invention showing a ribbed blade adapter sliding within a tubular shield.

The shield 40 is a cylindrical tube made of heat resistant plastic. The slider 38 is fixedly mounted to the cylindrical tube 40 for translatably moving the shield 40. The blade 42 may be fixedly mounted to the housing 14 and is positioned within the shield 40 as is shown herein. A slot 61 in the tube 40 may have a plastic or metal flange for fixedly holding the blade 42 to the housing 14 as the tube 40 is moved independently. Electrical power is applied to the flange and to the blade 42 thereon for cutting or coagulating as required. When the vacuum is applied air with plume flow through the tube 40 and this will lower the temperature therein. As a further embodiment, FIG. 10 partially shows a C-shaped shield 41 being hood-like the shield shown in FIG. 8. U.S. Pat. Nos. 7,241,294; 7,959,633; and 8,128, 622 being incorporated herein as noted above as to their teaching regarding the holding and operation of the blade illustrate the blade holding devices in pencils. As seen in FIG. 10, the blade 42 is mounted to a blade adapter 100 being held in a distal opening 108 of the housing 14 by a flange 110 therebetween. A proximal end 102 is fixedly mounted to the blade adapter 100 and further to the housing 14 by a flange device 104 such as a clip. Electrical feeds to the end 102 are not shown. Due to the requirement that the blade adapter 102 be firmly held in housing 14, a C-shaped shield 41 is mounted thereabout, with a cross section shown below. The open section 112 of the C-shaped shield 41 slides about the blade 42, adapter 100 and end 102, by the slider 38 attached to the shield 41 by an arm 106. These parts being heat resistant plastic. Sufficient space about the adapter 100 allows the plume to flow through when the vacuum is applied. FIG. 11 by front view of the surgical pencil 10 shows another embodiment of a tubular shield 40 that slides within a cylindrical hole 124 in the housing 14. The blade 42 is mounted to an adapter 121 such as shown in the prior art, but now includes multiple ribs 122 on the adapter 121 that slide on the inside of the tubular shield 40. This provides for centering of the blade 42 therein, this holds the blade firmly in the surgical pencil 10, and provides for a defined space around the adapter 121 for vacuum removal of the plume 120. The end 124 of the blade 42 is fixedly mounted in the housing 14 to receive electrical wires as well as to prevent unwanted movement. Since no object is blocking the sliding tubular shield 40, an arm is attached thereto at the proximal end and to the slider 38 as previously shown. The unblock length of the blade 42 to the end 124 would be sufficient to allow the tubular shield 40 to substantially cover the blade 42 and to be moved to an interior position where the blade 42 would be substantially exposed. This particular embodiment would be applicable to the versions of the surgical pencil 10 shown in FIGS. 1 to 4, for example.

Figure 8:
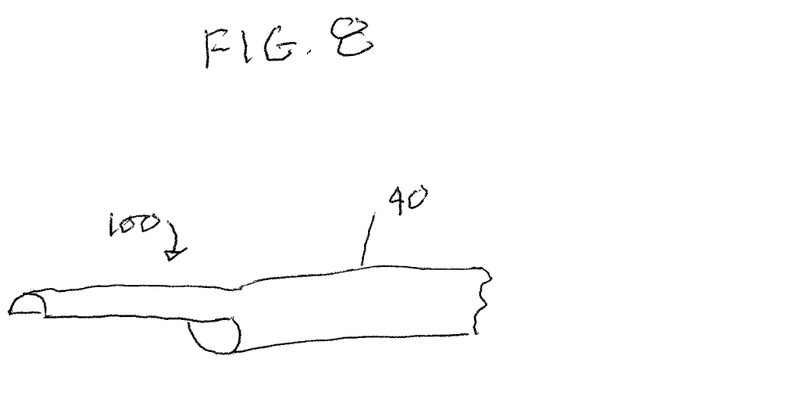
FIG. 8 is a partial side view of a shield having a hood thereover of the Present invention.
Figure 9:
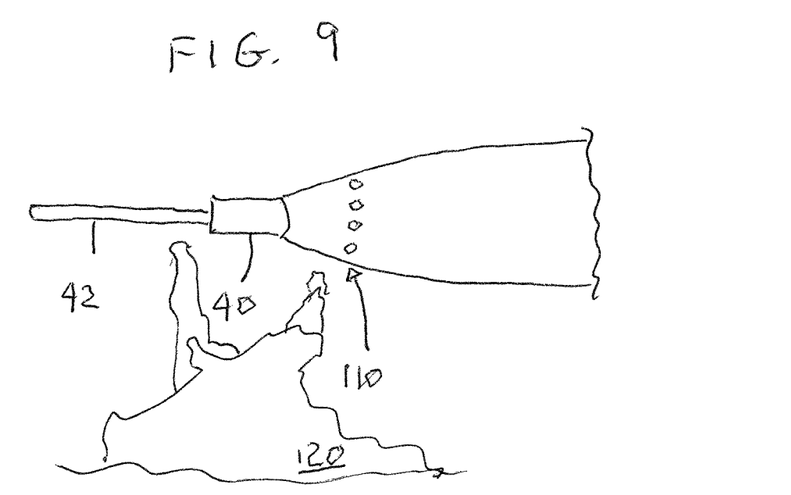
FIG. 9 is a partial side view of an elongated housing having supplement apertures for the removal of plume in addition to the shield 40 of the present invention.

FIG. 8 shows by a side view the tube/shield 40 having a hood section 100 thereon that will further aid in removing plume. The hood 100 may be integrally formed with the tube 40. FIG. 9 shows by side view the distal end of the pencil 10 with supplemental apertures 110 for removing plume 120 in addition to the shield 40. FIG. 7 further shows a filter 122 mounted in the vacuum line 22 being flexible tubing. The filter 122 would be removable since contamination from the plume 120 should not reach the vacuum source 24. Both the tubing 22, the surgical pencil 10, and the filter 122 would be disposable due to contamination from the plume 120.

The following is the method of using the present invention in a surgical setting where a patient is having a procedure:

providing the surgical pencil having an adjustable vacuum nozzle;

turning on the vacuum source of the surgical pencil;

adjusting the amount of vacuum by either adjusting a slider switch attached to the shield/nozzle to adjust the amount of vacuum; in an alternative embodiment, a vacuum control is attached to a vacuum line or surgical pencil wherein adjust of such changes the amount of vacuum through the shield/nozzle;

turning on the electrical power to the surgical pencil;

turning on an appropriate electrical power to a blade;

translating and retracting the shield/nozzle to the closed position to engage the vacuum source and thus substantially removing the shield from the blade; cutting and/or coagulation the human body where operated upon during either electrosurgical or laser surgery procedures;

using the surgical pencil to remove plume by vacuum through the vacuum nozzle;

turning off the vacuum source;

turning off the electrical power; and removing any contamination from the vacuum source and disposing of the surgical pencil when completed.

Since many modifications, variations, and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A surgical pencil, said surgical pencil comprising:
an elongated housing being capable of being held by one hand of an operator;
electrical means for powering said surgical pencil, said electrical means including a source of power and a control means operably connected, said source of power connected to said control means by one or more wires;
a vacuum source for providing a vacuum to said surgical pencil for removing a surgical plume, and a vacuum control for said vacuum source, said vacuum control including one or more switches; and
a shield for said surgical pencil, said shield movably mounted in said elongated housing, said shield comprising a cylindrical tube having a portion of a surgical blade therein in a proximal end, a slider switch fixedly mounted to said shield, said vacuum operably connected to said cylindrical tube for removing said surgical plume, said vacuum control having a disconnectable coupling in said elongated housing operably connected to said slider switch to turn on or turn off said vacuum and to further provide vacuum in a variable manner as desired by selectively moving said slider therebetween;
wherein a distal end of said flexible tubing has a separable coupling having a first coupling end being a seat for a conical male plug, said first coupling end mounted to a proximal end of said surgical pencil in an interior of said housing.

2. A surgical pencil, said surgical pencil comprising:
an elongated housing being capable of being held by one hand of an operator;
electrical means for powering said surgical pencil, said electrical means including a source of power and a control means operably connected, said source of power connected to said control means by one or more wires;
a vacuum source for providing a vacuum to said surgical pencil for removing a surgical plume, and a vacuum control for said vacuum source, said vacuum control including one or more switches; and
a shield for said surgical pencil, said shield movably mounted in said elongated housing, said shield comprising a cylindrical tube having a portion of a surgical blade therein in a proximal end, a slider switch fixedly mounted to said shield, said vacuum operably connected to said cylindrical tube for removing said surgical plume, said vacuum control having a disconnectable coupling in said elongated housing operably connected to said slider switch to turn on or turn off said vacuum and to further provide vacuum in a variable manner as desired by selectively moving said slider therebetween;
wherein a distal end of said flexible tubing has a separable coupling having a first coupling end being a seat for a conical male plug, said first coupling end mounted to a proximal end of said surgical pencil in an interior of said housing; and
wherein said shield has said cylindrical tube with a second end, said second end having a second coupling, a conical male plug, mounted thereon that removably fits within said first coupling, a seat, to allow a vacuum to flow therethrough in a controlled manner, said slider mounted to said cylindrical tube for translatably moving said shield with said conical male plug thereon, said slider translatably mounted in said housing.

3. A surgical pencil, said surgical pencil comprising:
an elongated housing being capable of being held by one hand of an operator;
electrical means for powering said surgical pencil, said electrical means including a source of power and a control means operably connected, said source of power connected to said control means by one or more wires;
a vacuum source for providing a vacuum to said surgical pencil for removing a surgical plume, and a vacuum control for said vacuum source, said vacuum control including one or more switches; and
a shield for said surgical pencil, said shield movably mounted in said elongated housing, said shield comprising a cylindrical tube having a portion of a surgical blade therein in a proximal end, a slider switch fixedly mounted to said shield, said vacuum operably connected to said cylindrical tube for removing said surgical plume, said vacuum control having a disconnectable coupling in said elongated housing operably connected to said slider switch to turn on or turn off said vacuum and to further provide vacuum in a variable manner as desired by selectively moving said slider therebetween; and
wherein said slider is able to be pushed forward and said shield thereon completely covers said blade in an off position.

4. A method of using a surgical pencil to remove a surgical plume, said method comprising the steps of:
providing the surgical pencil having an adjustable vacuum nozzle;
turning on the vacuum source of the surgical pencil;
turning on the electrical power to a blade;
adjusting a vacuum control within the surgical pencil by moving a slider that is fixedly attached to a shield partially about a blade of the pencil, the vacuum control having a disconnectable coupling in an elongated housing of the surgical pencil that is operably connected to the slider switch to turn on or off the vacuum and to further provide vacuum in a variable manner as desired by selectively moving said slider by adjusting a male plug to a seat;
substantially removing the shield from the blade;
cutting and/or coagulating a human body when operated upon during either electrosurgical or laser surgery procedures;
using the surgical pencil to remove plume by vacuum through the vacuum nozzle;
turning off the vacuum source;
turning off the electrical power; and
removing any contamination from the vacuum source and disposing of the surgical pencil when completed; and
further including moving the shield to completely cover the blade while vacuum suction is in an off position.

5. A surgical pencil, said surgical pencil comprising:
an elongated housing being capable of being held by one hand of an operator;
electrical means for powering said surgical pencil, said electrical means including a source of power and a control means operably connected, said source of power connected to said control means by one or more wires;
a vacuum source for providing a vacuum to said surgical pencil for removing a surgical plume, and a vacuum control for said vacuum source, said vacuum control including one or more switches; and a shield for said surgical pencil, said shield movably mounted in said elongated housing, said shield comprising a cylindrical tube having a portion of a surgical blade therein in a proximal end, a slider switch fixedly mounted to said shield, said vacuum operably connected to said cylindrical tube for removing said surgical plume, said vacuum control having a disconnectable coupling in said elongated housing operably connected to said slider switch to turn on or turn off said vacuum and to further provide vacuum in a variable manner as desired by selectively moving said slider therebetween; and wherein said blade is exposed and uncovered by said shield when said slider is in the rearward position and vacuum suction is engaged.

6. A method of using a surgical pencil to remove a surgical plume, said method comprising the steps of:

providing the surgical pencil having an adjustable vacuum nozzle;

turning on the vacuum source of the surgical pencil;

turning on the electrical power to a blade;

adjusting a vacuum control within the surgical pencil by moving a slider that is fixedly attached to a shield partially about a blade of the pencil, the vacuum control having a disconnectable coupling in an elongated housing of the surgical pencil that is operably connected to the slider switch to turn on or off the vacuum and to further provide vacuum in a variable manner as desired by selectively moving said slider by adjusting a male plug to a seat;

substantially removing the shield from the blade;

cutting and/or coagulating a human body when operated upon during either electrosurgical or laser surgery procedures;

using the surgical pencil to remove plume by vacuum through the vacuum nozzle;

turning off the vacuum source;

turning off the electrical power; and removing any contamination from the vacuum source and disposing of the surgical pencil when completed; and further including moving the slider that is fixedly attached to the blade shield into the rearward position in order to uncover and expose the blade in the on position.

* * * * *